(12) United States Patent
Leclercq

(10) Patent No.: US 7,632,312 B2
(45) Date of Patent: Dec. 15, 2009

(54) ARTIFICAL LUMBAR DISC

(75) Inventor: Toussaint Leclercq, New Orleans, LA (US)

(73) Assignee: Neurocare International, Inc., New Orleans, LA (US)

( * ) Notice: Subject to any disclaimer, the term of this patent is extended or adjusted under 35 U.S.C. 154(b) by 230 days.

(21) Appl. No.: 11/088,410

(22) Filed: Mar. 24, 2005

(65) Prior Publication Data

US 2006/0217810 A1    Sep. 28, 2006

(51) Int. Cl.
*A61F 2/44* (2006.01)
(52) U.S. Cl. ................... 623/17.12; 623/17.16
(58) Field of Classification Search .... 623/17.11–17.16
See application file for complete search history.

(56) References Cited

U.S. PATENT DOCUMENTS

| | | | |
|---|---|---|---|
| 4,349,921 A | 9/1982 | Kuntz | |
| 4,759,769 A | 7/1988 | Hedman et al. | |
| 4,863,477 A | 9/1989 | Monson | |
| 4,911,718 A * | 3/1990 | Lee et al. | 623/17.15 |
| 5,071,437 A | 12/1991 | Steffee | |
| 5,171,281 A | 12/1992 | Parsons et al. | |
| 5,258,031 A | 11/1993 | Salib et al. | |
| 5,314,477 A | 5/1994 | Marnay | |
| 5,458,642 A | 10/1995 | Beer et al. | |
| 5,534,030 A | 7/1996 | Navarro et al. | |
| 5,562,738 A | 10/1996 | Boyd et al. | |
| 5,683,465 A | 11/1997 | Shinn et al. | |
| 5,824,094 A | 10/1998 | Serhan et al. | |
| 5,861,041 A * | 1/1999 | Tienboon | 623/17.16 |
| 5,888,226 A | 3/1999 | Rogozinski | |
| 5,893,889 A | 4/1999 | Harrington | |
| 6,113,637 A | 9/2000 | Gill et al. | |
| 6,139,579 A | 10/2000 | Steffee et al. | |
| 6,156,067 A | 12/2000 | Bryan et al. | |
| 6,162,252 A | 12/2000 | Kuras et al. | |
| 6,296,664 B1 | 10/2001 | Middleton | |
| 6,315,797 B1 | 11/2001 | Middleton | |

(Continued)

FOREIGN PATENT DOCUMENTS

EP    1354572    10/2003

(Continued)

OTHER PUBLICATIONS

Lagrone M.O., Bradford, D.S. Moe, J. H., et al. Treatment of Symptomatic Flatback After Spinal Fusion, J. Bone Joint Surg 1988:70A:569-580.

(Continued)

*Primary Examiner*—Eduardo C Robert
*Assistant Examiner*—Ellen C Hammond
(74) *Attorney, Agent, or Firm*—Gauthier & Connors LLP

(57) ABSTRACT

An artificial lumbar disc made of three components which are inserted individually. Two bean shaped implants are a mirror image of each other and are designed to be inserted on each side of the disc cavity. The third component is designed to fill the disc cavity remaining after the first two components have been inserted. The unique design focuses on restoring the natural function of the disc, reestablishing a preferred disc space, and providing ease of insertion through both a posterior and anterior approach. Moreover, the potential of prosthesis failure is fully addressed and feasible solutions to such an occurrence are proposed.

20 Claims, 5 Drawing Sheets

U.S. PATENT DOCUMENTS

| | | | |
|---|---|---|---|
| 6,316,031 B1 | 11/2001 | Oshlack et al. | |
| 6,368,350 B1 | 4/2002 | Erickson et al. | |
| 6,395,032 B1 | 5/2002 | Gauchet | |
| 6,419,704 B1 | 7/2002 | Ferree | |
| 6,527,804 B1 | 3/2003 | Gauchet et al. | |
| 6,533,817 B1 * | 3/2003 | Norton et al. | 623/17.16 |
| 6,579,320 B1 | 6/2003 | Gauchet et al. | |
| 6,582,466 B1 | 6/2003 | Gauchet | |
| 6,582,786 B1 * | 6/2003 | Bonk et al. | 428/35.7 |
| 6,599,320 B1 * | 7/2003 | Kuslich et al. | 623/17.11 |
| 6,607,558 B2 * | 8/2003 | Kuras | 623/17.16 |
| 6,645,248 B2 * | 11/2003 | Casutt | 623/17.12 |
| 7,338,526 B2 * | 3/2008 | Steinberg | 623/17.12 |
| 2004/0133281 A1 * | 7/2004 | Khandkar et al. | 623/17.16 |
| 2004/0220672 A1 * | 11/2004 | Shadduck | 623/17.16 |
| 2004/0230309 A1 * | 11/2004 | DiMauro et al. | 623/17.12 |
| 2005/0027358 A1 | 2/2005 | Suddaby | |

FOREIGN PATENT DOCUMENTS

| | | |
|---|---|---|
| EP | 1354572 A | 10/2003 |
| FR | 2639823 | 12/1988 |
| WO | WO 91/00713 | 1/1991 |
| WO | WO 92/10982 | 7/1992 |
| WO | WO9210982 A | 7/1992 |
| WO | WO9423671 A | 10/1994 |
| WO | WO 94/23671 | 10/2003 |

OTHER PUBLICATIONS

Santos, E.G., Polly, Jr., D.W., Mehbod, A.A., Saleh, K.J. Disc Arthroplasty: Lessons Learned From Total Joint Arthroplasty, The Spine Journal 4 2004:182S-189S.

Lee, C.K., Goel, V.K. Artificial Disc Prosthesis, The Spine Journal 4 2004:209S-218S.

Bertagnoli B. Disc Surgery in Motion. SpineLine 2004:5:23-28.

Gunnar Andersson, B.J., Ortengren, R., Nachemson, A.L. The Sitting Posture: An Electromyographic and Discometric Study, Symp on the Lumbar Spine 1975:6:1:105-120.

Simmons, J.W. Posterior Lumbar Interbody Fusion (PLIF), The Adult Spine: Principles and Practice, 1991.

* cited by examiner

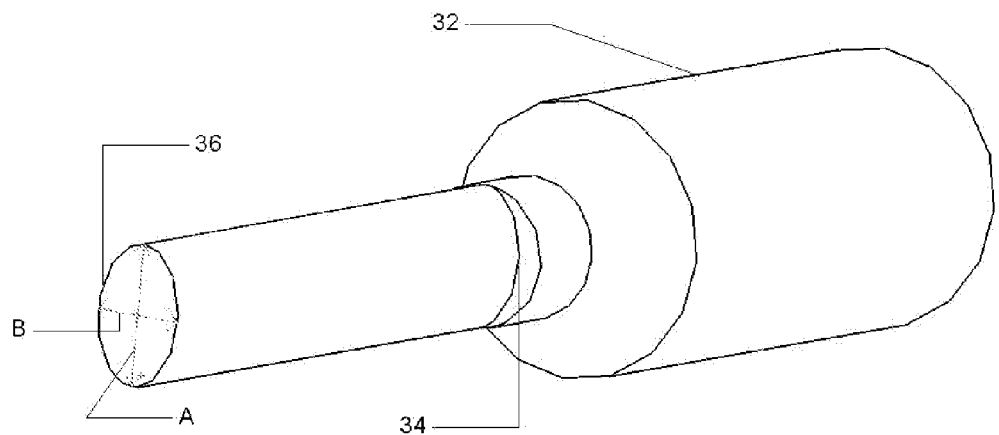
FIG. 7
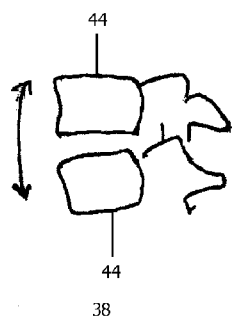 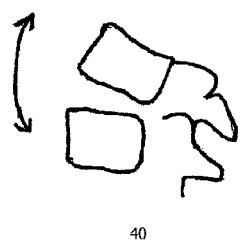 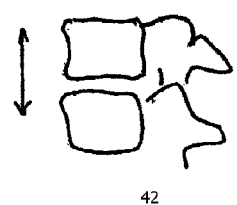
FIG. 8A     FIG. 8B     FIG. 8C

ARTIFICAL LUMBAR DISC

BACKGROUND OF THE INVENTION

1. Field of the Invention

This invention relates generally an artificial lumbar disc made of three components. The prosthesis is inserted into a disc cavity to restore natural function of the disc.

2. Description of the Prior Art

Back pain is the leading cause of disability and worker compensation claims in the US for people under 45 years of age. The cost of treating back pain varies according to different studies but numbers as high as $26 billion in direct cost and $90 billion in total cost are frequently cited.

The normal human disc is comprised of an outer fibrous structure (annulus fibrosus) with fibrous bands organized like the plies of a radial tire. The annulus fibrosus controls the motion of the vertebral segment. The inner core or nucleus pulposus has a water content of 70 to 85%. It transmits and dampens axial loading ("shock absorbing" function). In degenerative disc disease, the annulus develops structural lesions that weaken its ability to control segmental movements and to contain the central core. Also, the nucleus loses part of its water content. The combined results provide for segmental instability and a decrease in the shock absorbing function of the disc. Spinal stenosis, osteophyte formation, disc herniation, and possible nerve root compression are associated with disabling back pain.

At the present time, when conservative measures fail to provide relief for the patient, the most common available surgical procedures consist of discectomy (in variable amount of completeness) or arthrodesis (spinal fuision) of the involved segment. Though initially successful in relieving pain in 50 to 90% of cases, many discectomy patients experience return of pain and may require additional surgery, often in the form of a spinal fusion. Arthrodesis techniques provide for stability of the affected segment and solid fusions are now reported in the 90 to 95% range though pain relief is present in only 75 to 80% of cases depending on the series reported. Unfortunately, as longer follow-up studies become available, accelerated degeneration of the unfused segments above and below the arthrodesis presents an increasing problem.

Spinal surgeons have become progressively more aware of this phenomenon, opening the door for new techniques that can preserve the motion of the vertebral segment with artificial disc prostheses. This has resulted in a more physiological approach to intervertebral disc disease. Artificial disc prostheses are now in different stages of development. At the present time, only one artificial disc has been approved for patient use in the US. It has a ball and socket design, requires a major invasive surgical procedure, and does not address the issue of the "shock absorbing" function of the normal human intervertebral disc. Other prostheses now at different stages of development are also of the ball and socket design and/or require major invasive surgery for adequate implantation.

SUMMARY OF THE INVENTION

There is a need for newer prosthetic designs that will provide an artificial disc with components more similar to the natural disc, allowing for reestablishment of a more physiologically correct function. There is also a need for designs that allow for less invasive surgery for their insertion thus providing patients with safer alternatives. In addition and importantly, the present state of the art does not provide for a safe, reproducible salvage operation in the case of prosthetic failure. The present invention provides answers to the multiple problems cited above.

Generally, an artificial lumbar disc prosthesis can be formed from three components. Each of the components may be inserted individually. Two bean shaped implants are a mirror image of each other and are designed to be inserted on each side of the disc cavity. The third component is designed to fill the remaining disc cavity after the first two components have been inserted. The unique design focuses on restoring the natural function of the disc, reestablishing a preferred disc space, and providing ease of insertion through both a posterior and anterior approach. Moreover, the potential of prosthesis failure is fully addressed and feasible solutions to such an occurrence are proposed.

These and other features and objectives of the present invention will now be described in greater detail with reference to the accompanying drawings, wherein:

BRIEF DESCRIPTION OF THE DRAWINGS

FIG. 7 is a perspective view of the dilator used to dilate the disc space in order to obtain an ideal height.
FIGS. 8A-C are perspective views of the different variations of lordosis.

DETAILED DESCRIPTION OF THE INVENTION

As used herein, the following definitions apply. In the context of this application, the word anterior is meant to apply to that aspect of the spine facing the abdomen of the patient. The word posterior is meant to apply to that aspect of the spine facing the back of the patient.

Figure 1:
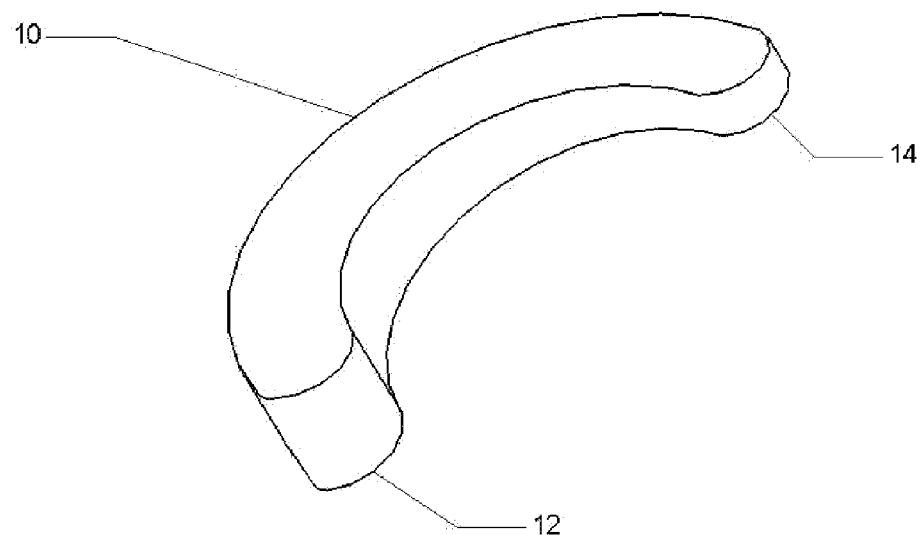
FIG. 1 is a perspective view of the bean shaped implant.
Figure 2:
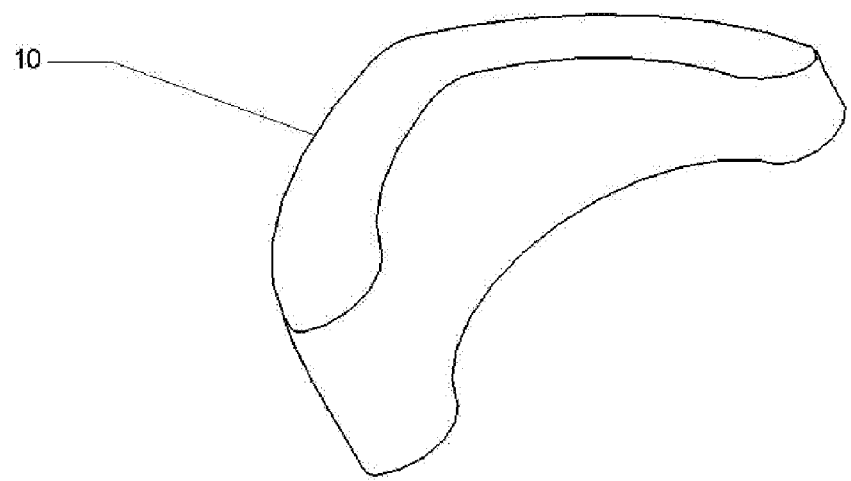
FIG. 2 is a perspective view of the bean shaped implant.

FIG. 1 shows a perspective view of a bean shaped implant 10 which illustrates the difference in height between the anterior and posterior sides. As shown the thickness of the anterior side 12 of the implant is larger than the posterior side 14. The convexity of the bean shaped implant 10 as illustrated in FIG. 2. These physiological characteristics are key to mimicking the natural juxtaposition and movements of the disc and vertebral endplates. This uniquely allows the implants be built to individual specifications to suit the individual patient. In particular, the vertebral endplates are not parallel in the normal disc space, therefore the prosthesis is designed with the anterior aspect thicker than the posterior aspect. The normal disc space is bi-concave and thus both the inferior and superior surfaces of the bean shaped implants facing the vertebral endplates must be convex. Furthermore, in the present invention, the difference in thickness as well as the convexity between the anterior and posterior part of the bean shaped prosthesis is variable and can be adjusted to individual patient needs. The exact and varying degrees of convexity a cross the implant are obtained through radiological graphing. The further advantages of the bean shaped implant shall be apparent when we discuss surgical techniques and the biomechanical properties of the implant.

Figure 3:
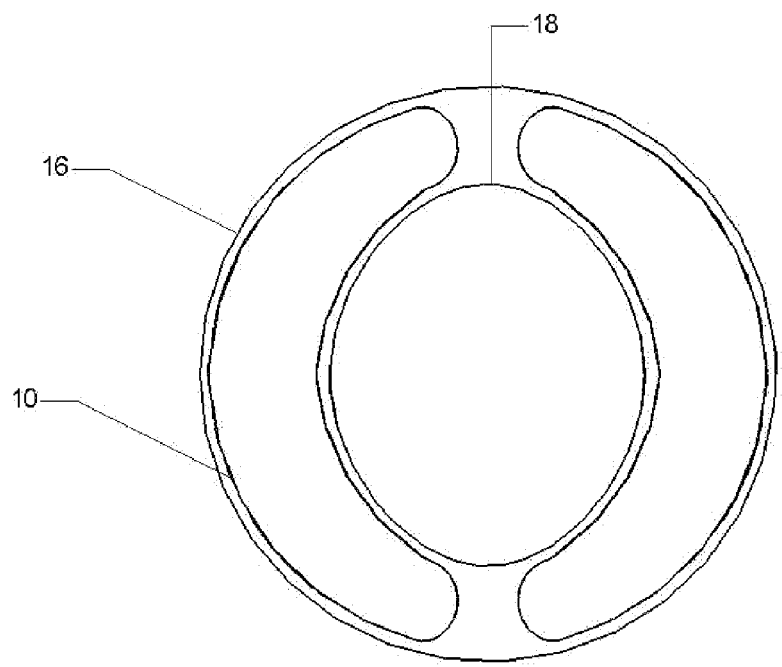
FIG. 3 is a top view of all three components after insertion.
Figure 4:
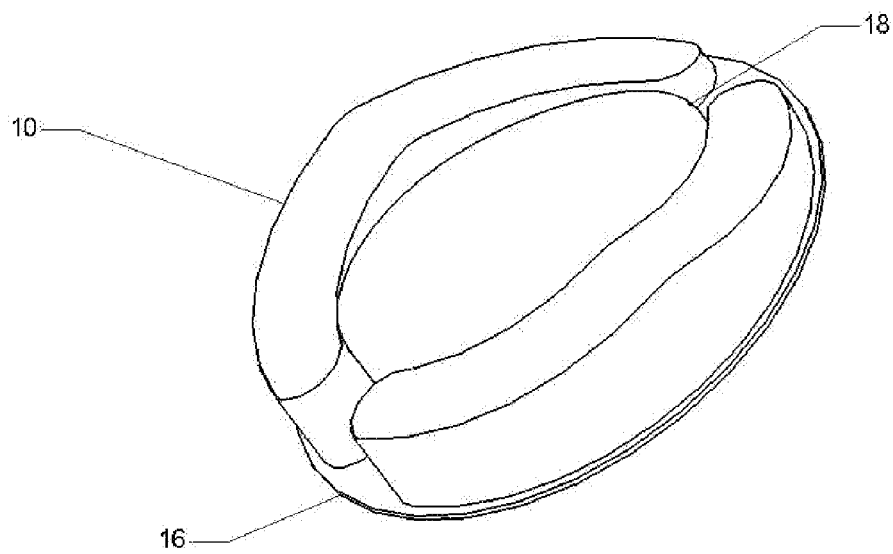
FIG. 4 is a perspective view of all three components after insertion.

FIG. 3 is a top view and FIG. 4 is a perspective view showing all three components after insertion. One of the bean shaped implants 10 is meant to be inserted on the left side and the second is inserted on the right side. Because of the design, the prosthesis can be inserted through a posterior as well as an anterior approach using techniques that are familiar to spine surgeons. The part of the annulus fibrosus 16 which is left intact supports the containment of the prosthesis and lessens the chances of migration.

The central inflatable nucleus 18 of the artificial disc is to occupy the disc space left empty between the two afore mentioned implants 10. The size of the midline implant can be chosen using pre-operative measurements to fill adequately the existing cavity. When completely inflated, the implant shall fill the cavity completely, maximizing areas of contact between the prosthesis and the end plates thus minimizing the chance of subsidence or migration.

The midline implant 18 consists of a membrane, which can be inserted on top of an inserting tool. Once in place, the midline implant can be filled under pressure with liquid gel, gas, polymer, or any other biocompatible material. The pressure inside the implant can be regulated and optimized. The central implant 18 has a detachable catheter, that is preferably attached at the time of insertion. Once the implant is in place, the catheter used to inflate the device can be removed, leaving the (one-way valve) implant in place. The inflatable implant, when totally expanded, locks in place the other components of the prosthesis, eliminating or at least significantly reducing the chances of migration.

The body of the prosthesis is made of a silastic material or any other biocompatible material of adequate consistency, resiliency, flexibility, and compressibility. These characteristics are necessary to provide adequate constrain in flexion—extension, lateral tilt, rotation, and axial loading, thus mimicking the natural intervertebral disc.

Figure 5:
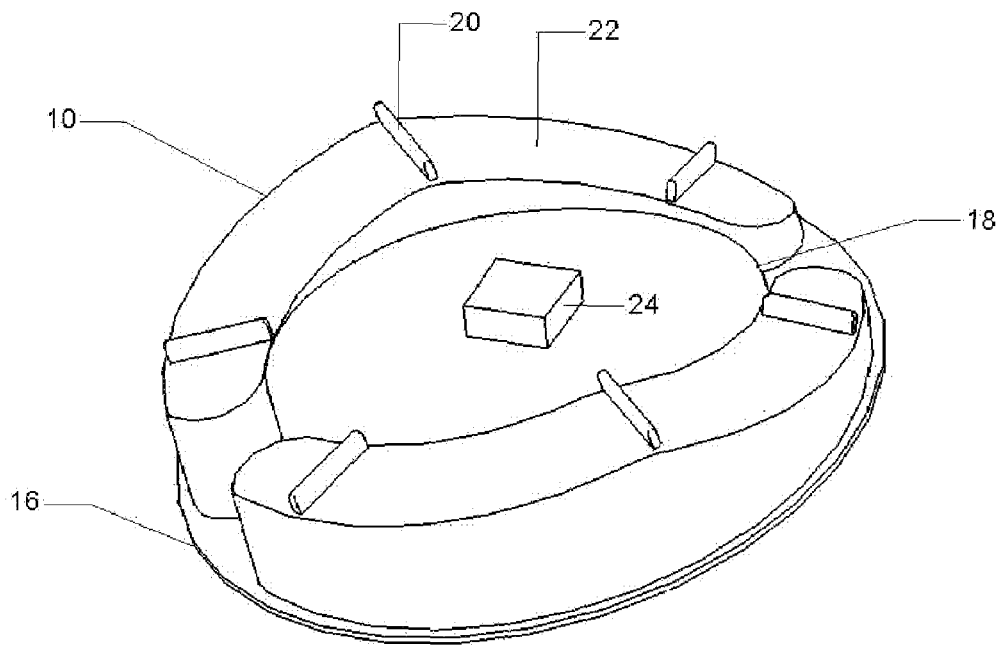
FIG. 5 is a perspective view of all three components after insertion including the fins which ensure attachmnent.

FIG. 5 illustrates the complete prosthesis including metal fins 20 which ensure satisfactory attachment to the vertebral endplates and prevents migration. The fins 20 are part of a metal plate 22 which inferior and superior surfaces of the endplates of the bean shaped implant 10. The plates 22 and fins 20 are made of medical grade, porous titanium alloy or any other metal porcelain, or other synthetic material. The metal plates have at least two fins facing the endplates to prevent displacement. Alternatively porous titanium may be sprayed on the surface of the implant 10 or metal having "memory" may be used. When using a metal with a memory, the fins on the plate are reduced such that they are smooth and "flat" on the metal surface. Once the implant including the metal is placed in the body and the temperature if the same increases, the fins "grow" and "develop" on the plate to resume their previous shape.

In another embodiment, a pressure monitor 24 may be inserted in the midline implant to allow for post-operative intradiscal pressure measurement.

In yet another embodiment of this invention, the surfaces of the bean shaped prostheses facing the vertebral endplates are coated with porous titanium.

In yet another embodiment of this invention, the surfaces of the midline implant facing the vertebral endplates are coated with porous titanium.

In yet another embodiment of this invention, the inferior and superior surfaces of the bean-shaped implant are made of memory titanium alloy allowing for full expansion of the fins after implantation.

SURGICAL TECHNIQUE

The surgical techniques used for insertion of the prosthetic disc are similar to the techniques used universally by spine surgeons to insert paired implants for the purpose of fusing the spine, which include both:

(ALIF—Anterior lumbar interbody fusion)
(PLIF—Posterior lumbar interbody fusion).

Because these procedures are familiar to spine surgeons, their description shall not be repeated except to describe a few modifications that have been designed to accommodate the insertion of this artificial disc along with specially designed instruments to make the technique user friendly.

Figure 6:
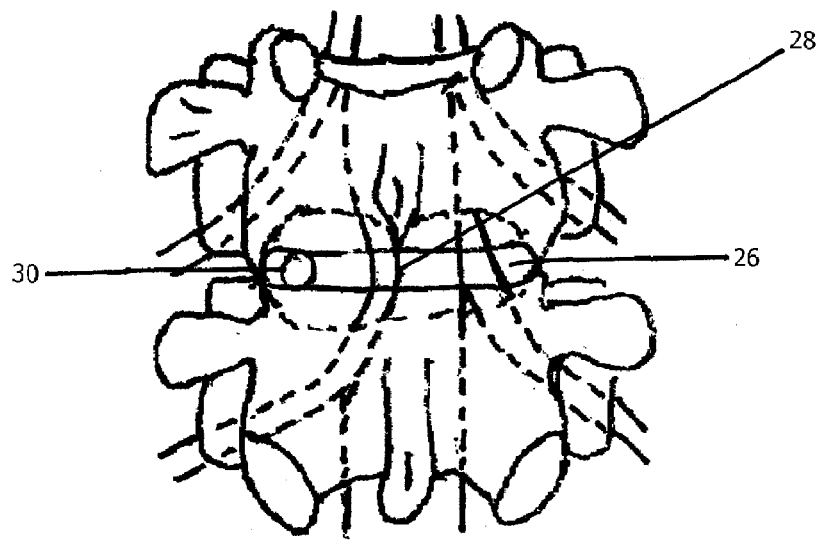
FIG. 6 is a perspective view of the posterior of the human spine.

FIG. 6 shows the posterior of the human spine where the surgical procedure is performed. Once the intervertebral disc 26 has been approached, a small incision is made on one side of the disc and then the other. The nervous structures 28 can be safely retracted as long as the two sides are approached one after another. The nervous structures should not be retracted over the midline. The disc material is then removed thoroughly through the two openings 30 using accepted techniques.

In degenerative disc disease, the disc height is usually reduced when compared with normal values. Using an algorithm that we have developed the ideal disc space height for the level involved is established. By using dilators specially designed for this purpose and inserting them in a sequential fashion from left to right, the disc space can be reestablished to its normal pre-diseased values before inserting the artificial disc.

FIG. 7 shows a specially designed dilator used to reestablish the disc space. It consists of a handle 32, release mechanism 34, and detachable tip 36. The detachable tip 36 has an elliptical shape with large diameter A and small diameter B. The large diameter A and small diameter B differ by 1 mm. A quarter turn of the dilator provides an increase of 1 mm in the disc space height. A set of dilators allows for the progressive increase of the disc height until satisfactory pre-disease values are established.

The two bean shaped lateral prostheses 10 are then inserted and the midline prosthesis 18 inflated to a satisfactory pressure, locking the components of the prosthesis in place. The closure may then proceed.

The surgical techniques described above are only meant to provide an example of a technique that can be used to insert this artificial disc. Other techniques that provide for a safe and adequate exposure of the intervertebral disc may be used including percutaneous approaches or endoscopic surgery.

Due to its design, the present invention allows for flexion, extension, lateral tilt, rotation, and also allows for axial loading (shock absorber function), contrary to the ball and socket designs presently available.

Figure 9:
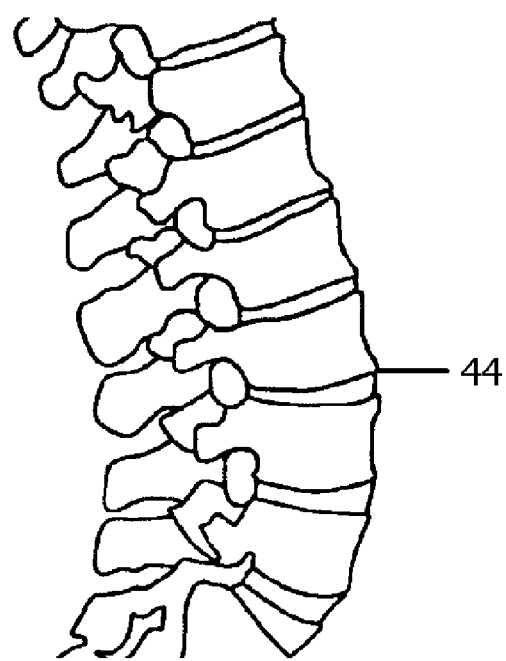
FIG. 9 is a perspective view of the lumbar section of the spine.

Because the invention has two bean shaped implants 10 of various heights, it allows for reestablishment or preservation of the lumbar lordosis contrary to existing devices that have parallel surfaces facing the endplates. In the normal human disc, the vertebral endplates are not parallel resulting in the fact that the anterior aspect of the disc is higher than the posterior aspect. FIGS. 8A-C illustrates the amount of lordosis which uniquely varies among individual patients. These amounts are normal lordosis 38, extreme lordosis 40, and the loss of lordosis 42 which results in "flat back" syndrome. As illustrated by the normal lordosis 38 in FIG. 8 and also by FIG. 9, the lumbar section of the spine has a natural curvature. This curvature is the reason why the verterbral endplates 44 are not parallel. Existing artificial discs have anterior and posterior heights which are the same, not taking into consideration the normal anatomy of the human disc. This prosthesis addresses this issue.

The loss of lordosis results in back pain and junctional degeneration (this is precisely what the artificial disc is supposed to prevent). Therefore, the prosthesis and the surgical technique are designed in a manner in which to duplicate the pre-disease lordotic conditions. 90% of patients with flat back complain of back pain. Lack of lordosis results in detrimental stresses on the adjacent vertebral segment accelerating degenerative changes and creating back pain. Increase in intradiscal pressure has been associated with hypolordotic conditions. Spinal alignment should be preserved or restored, especially sagittal lordosis.

Because of the design of this artificial disc, the ease of insertion allows for a posterior surgical approach to the lumbar spine contrary to existing prosthesis which require an anterior approach. The anterior approach is plagued with a number of iatrogenic complications including retrograde ejaculation in males, severe bleeding requiring extensive transfusions, vessel injury, thrombosis with possible embolization, long term venous insufficiency, and urethral injury. Deaths have been reported due to such complications. These iatrogenic problems have concerned surgeons to the extent that it limits the indications for surgery. Low back pain is not a fatal condition and the surgeons have to consider the risk-benefit ratio of the anterior approach.

It should be emphasized that the design of this invention allows for anterior as well as posterior insertion. Another advantage of the design is that the surgical techniques used (allowing for some modifications) are familiar to spine surgeons, avoiding the "learning curve" inherent to new instrumentation.

Because the incisions in the annulus are minimal, a significant amount of the annulus is left intact, providing containment of the artificial disc. This will eliminate, or at least significantly decrease the risk of migration of the prosthesis. The anterior surgical approach used for insertion of the presently available total disc prostheses makes preservation of the anterior annulus and the anterior longitudinal ligament impossible or very unlikely.

Advantageously, with this design, the unique combination of two lateral bean shaped implants with an inflatable center results in a complete filling of the cavity left by the disc removal. This tight fit of the implants within the disc space argues favorably for a stable construct with little or no likelihood of migration.

A further advantage of this invention is that the prosthesis can be "custom made" allowing for variable anterior and posterior thickness as well as for varying degrees of convexity thus allowing for a more physiologically correct outcome. A person's disc area is modeled and then the prosthesis is formed to fit that individual's disc area.

The issue of prosthesis failure is commonly left unaddressed even though these prosthesis are destined to remain in place for many years and even decades. None of the prosthetic designs of total disc prosthesis have known specific considerations for replacement or revision.

With this prosthesis design, a failure of the artificial disc to function can be addressed by deflating and removing the central prosthesis, then filling the cavity with bone to obtain an interbody lumbar fusion, an operation that is well accepted and has a satisfactory historical track record. This issue once again highlights the benefits of a posterior approach since the following risks associated with the reopening of an anterior approach are greater. Reopening of an anterior, transabdominal approach carries significant risk of severe complications with possible intractable bleeding due to adhesions to the major blood vessels and is a life threatening operation.

Though this invention is designed to be applied to the treatment of the human lumbar spine, it may be applied to other vertebrates of the animal kingdom.

In light of the foregoing, it will now be appreciated by those skilled in the art that various changes may be made to the embodiment herein chosen for purposes of disclosure without departing from the inventive concept defined by the appended claims. Non-limiting examples of such changes including using an endoscopic procedure in a variant of the technique, varying the number of fins on the implants, or using polymers, nitrous oxide or a hydro gel to inflate the central implant.

The invention claimed is:

1. A prosthetic lumbar disc adapted to be inserted into a disc cavity, said disc cavity having an annulus and vertebral plates along a substantially horizontal plane of a disc cavity, comprising:

A. a pair of separate, independent bean shaped implants consisting of a first bean shaped implant and a second bean shaped implant, each of said first and second independent bean shaped implants comprising a bone contacting surface and an annulus contacting surface and each implant being flexible and having a varying thickness according to the natural contour of the annulus and vertebral plates, whereby each of said first and second independent bean shaped implants have a first end which is opposite to a contralateral first end and a second end which is opposite to a contralateral second end and are adapted, after being inserted into a disc cavity, for being distant from each other, such that each of said separate independent bean shaped implants are at opposite ends of the vertebral body, so as to define:

free spaces extending between the first end of the first bean shaped implant and the first end of the second bean shaped implant located adjacent to the first end of the first bean shaped implant and extending between the second end of the first bean shaped implant and the second end of the second bean shaped implant located adjacent to the second end of the first bean shaped implant, and a disc space; and B. a nucleus comprising a midline inflatable implant which is insertable into the disc space defined between the first and the second independent bean shaped implants after being inserted into the disc cavity, through a free space extending between ends of the pair of independent bean shaped implants, said nucleus after being inserted into the disc space and after being inflated, being adapted for completely filling the space between the first and the second bean shape implant, and locking the first and second bean shaped implants in place in the lateral aspects of the disc cavity to form a prosthetic disc.

2. The prosthetic lumbar disc of claim 1, said bean shaped implants have upper and lower surfaces such that a granular porous titanium is applied to both the upper and lower surfaces of the bean shaped implants and the midline implant to ensure long term fixation to the vertebral end plates.

3. The prosthetic lumbar disc of claim 1 wherein each implant of the prosthetic lumbar disc is adapted for being inserted sequentially in the disc cavity.

4. The lumbar disc of claim 1, wherein the implants are adapted for being inserted individually and assembled in an intervertebral space.

5. The lumbar disc of claim 1, wherein the implants are adapted for being inserted through a posterior or an anterior approach to the disc cavity.

6. The lumbar disc of claim 1, wherein the first and second bean shaped implants are adapted to protect or reestablish a lordosis of a lumbar spine.

7. The lumbar disc of claim 1, wherein the first and second bean shaped implants are formed to fit unique contours of vertebral endplates.

8. The lumbar disc of claim 1, wherein the first and second bean shaped implant each have a height and convexity, such that the height and degree of convexity of the bean shaped implants are obtained through radiological and mathematical methods.

9. The lumbar disc of claim 1, wherein the implants are sequentially introduced into the disc space through a minimally invasive procedure.

10. The lumbar disc of claim 1, wherein a desired disc height can be reestablished through spinal dilators which allow for a progressive distracting of the disc cavity.

11. The lumbar disc of claim 1, wherein the degree of inflation of the midline implant can be controlled and optimized to obtain a physiologically correct implant.

12. The lumbar disc of claim 1, wherein a revision or salvage operation is performed in case of prosthesis failure.

13. The lumbar disc of claim 1, wherein the pair of bean shaped implants include metal upper and lower surfaces.

14. The lumbar disc of claim 13, wherein the metal upper and/or lower surfaces of each bean shaped implant includes at least two fins.

15. The lumbar disc of claim 1, wherein the first and second bean shaped implants are substantially mirror images of each other, one bean shaped implant on the left and one bean shaped implant on the right of the midline implant.

16. The lumbar disc of claim 1, wherein the bean shaped implants are inserted on the left and right side of a disc cavity, prior to the insertion of the nucleus, such that the first and second implant partly fill the disc cavity, and are adapted for being locked in place into said disc cavity by the nucleus after the midline inflatable implant being inflated for completely filling the disc space defined between the first and second bean shaped implants.

17. The prosthetic lumbar disc of claim 1, wherein the prosthetic disc preserves motion of a spinal disc.

18. The prosthetic lumbar disc of claim 1, wherein each implant remains flexible after insertion.

19. A modified posterior lumbar interbody method to insert an artificial implant in a patient, said artificial implant being adapted to be inserted into a disc cavity, wherein said disc cavity has a pre-disease height, comprising:
   A. a pair of independent bean shaped implants consisting of a first bean shaped implant and a second bean shaped implant, said first and second independent bean shaped implant comprising each a bone contacting surface and an annulus contacting surface and each implant being flexible and having a varying thickness according to the natural contour of the annulus, whereby said first and second independent bean shaped implant have each a first end and a second end opposite to the first end, whereby said first and second independent bean shaped implants are adapted, after being inserted into a disc cavity, for being distant from each other so as to define:
   a free space extending between the first end of the first bean shaped implant and the first end of the second bean shaped implant located adjacent to the first end of the first bean shaped implant located adjacent to the first end of the first bean shaped implant and a free space extending between the second end of the first bean shaped implant and the second end of the second bean shaped implant located adjacent to the second end of the first bean shaped implant, and
   a disc space; and
   B. a nucleus comprising a midline such that the midline is from left to right inflatable implant which is insertable into the disc space defined between the two independent bean shaped implants after being inserted between the disc cavity, through a free space extending between ends of a pair of independent bean shaped implants, said nucleus after being inserted into the disc space and after being inflated, being adapted for completely filling and locking the first and second bean shaped implants in place, on each side of the disc cavity
said method comprising:
progressively enlarging a disc cavity to its pre-disease height using spinal dilators;
preserving a physiological lordosis of a lumbar spine;
inserting the first and second bean shaped implants, to fit the physiological lordosis of an individual patient and natural concavity of an individual's vertebral end plates whereby said first and second independent bean shaped implants are distant from each other and define:
   (1) a first free space extending between the first end of the first bean shaped implant and the first end of the second bean shaped implant located adjacent to the first end of the first bean shaped implant and
   (2) a second free space extending between the second end of the first bean shaped implant and the second end of the second bean shaped implant located adjacent to the second end of the first bean shaped implant, and
   (3) a disc space;
inserting an expandable central implant into the disc space defined between the first and second bean shaped implants through a free space for ensuring a tight fit to further decrease any risk of implant migration; and
inflating the expandable central implant to give a prosthetic disc its final appearance, whereby said inflated central implant completely fills and locks the first and second bean shaped implants in place in the lateral aspects.

20. The method of claim 19, further comprising controlling and measuring a pressure inside a central portion of the artificial implant to optimize function of the implant and obtain a physiologically correct result.

* * * * *